(12) United States Patent
Kakade

(10) Patent No.: US 8,517,009 B2
(45) Date of Patent: Aug. 27, 2013

(54) METHODS AND APPARATUS FOR DELIVERING AEROSOLIZED MEDICATION

(75) Inventor: Prashant Kakade, Sunnyvale, CA (US)

(73) Assignee: MAP Pharmaceuticals, Inc., Mountain View, CA (US)

( * ) Notice: Subject to any disclaimer, the term of this patent is extended or adjusted under 35 U.S.C. 154(b) by 852 days.

(21) Appl. No.: 12/460,119

(22) Filed: Jul. 13, 2009

(65) Prior Publication Data

US 2010/0006096 A1 Jan. 14, 2010

Related U.S. Application Data

(60) Provisional application No. 61/134,804, filed on Jul. 13, 2008, provisional application No. 61/201,362, filed on Dec. 9, 2008.

(51) Int. Cl.
*B05B 1/26* (2006.01)
*A61M 15/00* (2006.01)

(52) U.S. Cl.
CPC ............... *A61M 15/009* (2013.01); *B05B 1/26* (2013.01)
USPC ............ 128/200.18; 128/203.12; 128/203.15; 128/203.19

(58) Field of Classification Search
USPC ............. 128/200.18, 200.23, 203.12, 203.15, 128/203.19
See application file for complete search history.

(56) References Cited

U.S. PATENT DOCUMENTS

| | | | |
|---|---|---|---|
| 2,305,210 A | 12/1942 | Wahlin | |
| 2,751,252 A | 6/1956 | Wahlin et al. | |
| 2,984,420 A | 5/1961 | Hession, Jr. | |
| 3,072,346 A | 1/1963 | Wahlin et al. | |
| 3,240,431 A | 3/1966 | Hug et al. | |
| 3,385,295 A | 5/1968 | Beasley | |
| 3,406,913 A | 10/1968 | Frangos | |
| 3,456,644 A | 7/1969 | Thiel | |
| 3,522,806 A | 8/1970 | Szekely | |
| 3,636,949 A | 1/1972 | Kropp | |
| 3,658,059 A | 4/1972 | Steil | |
| 3,838,686 A | 10/1974 | Szekely | |
| 4,049,200 A | 9/1977 | Sobol et al. | |
| 4,414,972 A | 11/1983 | Young et al. | |
| 4,429,835 A | 2/1984 | Brugger et al. | |
| 4,534,343 A | 8/1985 | Nowacki et al. | |
| 4,739,754 A | 4/1988 | Shaner | |
| 4,768,717 A | 9/1988 | Shay | |

(Continued)

FOREIGN PATENT DOCUMENTS

| | | |
|---|---|---|
| CA | 2086737 A1 | 1/1992 |
| DE | 89 12 098 U1 | 11/1990 |

(Continued)

OTHER PUBLICATIONS

European Search Report mailed on Oct. 7, 2005, for European Patent Application No. 05 07 6801 filed on Jul. 31, 1998, eight pages.

(Continued)

*Primary Examiner* — Annette Dixon
*Assistant Examiner* — Aundria Hairell
(74) *Attorney, Agent, or Firm* — Jennifer C. Cheng

(57) ABSTRACT

A pulmonary drug delivery device having one or more vortexing elements which impart beneficial flow characteristics to an inspiratory air flow carrying a medicament into the patient's lungs.

16 Claims, 9 Drawing Sheets

(56) References Cited

U.S. PATENT DOCUMENTS

| | | |
|---|---|---|
| 4,907,583 A | 3/1990 | Wetterlin et al. |
| 4,940,051 A | 7/1990 | Lankinen |
| 4,945,929 A | 8/1990 | Egilmex |
| 5,027,806 A | 7/1991 | Zoltan et al. |
| 5,027,808 A | 7/1991 | Rich et al. |
| 5,040,527 A | 8/1991 | Larson et al. |
| 5,054,477 A | 10/1991 | Terada et al. |
| 5,060,643 A | 10/1991 | Rich et al. |
| 5,067,655 A | 11/1991 | Farago et al. |
| 5,069,204 A | 12/1991 | Smith et al. |
| 5,115,981 A | 5/1992 | Callahan et al. |
| 5,178,138 A | 1/1993 | Walstrom et al. |
| 5,184,761 A | 2/1993 | Lee |
| 5,224,472 A | 7/1993 | Pesenti et al. |
| 5,228,624 A | 7/1993 | Mensink |
| 5,301,666 A | 4/1994 | Lerk et al. |
| 5,309,900 A | 5/1994 | Knoch et al. |
| 5,347,998 A | 9/1994 | Hodson et al. |
| 5,415,162 A | 5/1995 | Casper et al. |
| 5,435,297 A | 7/1995 | Klein |
| 5,458,135 A | 10/1995 | Patton et al. |
| 5,474,059 A | 12/1995 | Cooper |
| 5,520,166 A | 5/1996 | Ritson et al. |
| 5,549,101 A | 8/1996 | Trofast et al. |
| 5,577,497 A | 11/1996 | Mecikalski et al. |
| 5,590,645 A | 1/1997 | Davies et al. |
| 5,598,836 A | 2/1997 | Larson et al. |
| 5,615,670 A | 4/1997 | Rhodes |
| 5,617,845 A | 4/1997 | Poss et al. |
| 5,676,130 A | 10/1997 | Gupte et al. |
| 5,724,986 A | 3/1998 | Jones, Jr. et al. |
| 5,860,416 A | 1/1999 | Howlett |
| 5,875,774 A | 3/1999 | Clementi et al. |
| 5,894,995 A | 4/1999 | Mazzei |
| 5,896,853 A | 4/1999 | Howlett |
| 5,954,047 A | 9/1999 | Armer et al. |
| 6,026,808 A | 2/2000 | Armer et al. |
| 6,062,214 A | 5/2000 | Howlett |
| 6,095,141 A | 8/2000 | Armer et al. |
| 6,098,619 A | 8/2000 | Britto et al. |
| 6,367,471 B1 | 4/2002 | Genosar et al. |
| 6,638,495 B2 | 10/2003 | Weers et al. |
| 6,669,176 B2 | 12/2003 | Rock |
| 6,681,768 B2 | 1/2004 | Haaije de boer et al. |
| 2006/0185672 A1 | 8/2006 | Pinon et al. |
| 2006/0191534 A1* | 8/2006 | Hickey et al. ............ 128/203.15 |
| 2007/0209661 A1 | 9/2007 | Smyth et al. |

FOREIGN PATENT DOCUMENTS

| | | |
|---|---|---|
| EP | 0 237 507 A1 | 9/1987 |
| EP | 0 237 507 B1 | 9/1987 |
| EP | 0 261 649 B1 | 1/1992 |
| EP | 0 261 649 B2 | 1/1992 |
| EP | 0 363 060 B1 | 4/1994 |
| EP | 0 839 544 B1 | 5/1998 |
| EP | 0 911 048 A2 | 4/1999 |
| EP | 0 911 048 A3 | 4/1999 |
| EP | 0 911 048 B1 | 4/1999 |
| GB | 1 253 221 | 11/1971 |
| GB | 1 269 811 A | 4/1972 |
| GB | 2 279 879 A | 1/1995 |
| JP | 62-221366 A | 9/1987 |
| JP | 63-077460 A | 4/1988 |
| JP | 55-05968 A | 9/1993 |
| JP | 2927541 B2 | 5/1999 |
| WO | WO-90/10470 A1 | 9/1990 |
| WO | WO9211048 | 7/1992 |
| WO | WO-93/00951 A1 | 1/1993 |
| WO | WO-97/25086 A2 | 7/1997 |
| WO | WO-97/25086 A3 | 7/1997 |
| WO | WO-99/20331 A1 | 4/1999 |

OTHER PUBLICATIONS

European Search Report mailed on Dec. 3, 2009, for European Patent Application No. 05 07 6802, filed on Jul. 31, 1998, five pages.

International Preliminary Examination Report mailed on Jan. 27, 2011, for PCT Application No. PCT/US2009/004064, filed on Jul. 13, 2009, seven pages.

International Preliminary Examination Report mailed on Jan. 20, 2000, for PCT Application No. PCT/US98/21667, filed Oct. 15, 1998, ten pages.

International Preliminary Examination Report mailed on Jan. 1, 2002, for PCT Application No. PCT/US00/41722, filed Nov. 1, 2000, eight pages.

International Search Report mailed on Apr. 12, 1999, for PCT Patent Application No. PCT/US98/21667, filed on Oct. 15, 1998, six pages.

International Search Report mailed on Jun. 22, 2001, for PCT Patent Application No. PCT/US00/41722, filed on Nov. 1, 2000, two pages.

International Search Report mailed on Sep. 4, 2009, for PCT Patent Application No. PCT/US09/04064, filed on Jul. 13, 2009, one page.

Written Opinion mailed on Sep. 4, 2009, for PCT Application No. PCT/US09/04064, filed on Jul. 13, 2009, five pages.

Written Opinion mailed on Sep. 17, 1999, for PCT Application No. PCT/US98/21667, filed on Oct. 15, 1998, six pages.

* cited by examiner

METHODS AND APPARATUS FOR DELIVERING AEROSOLIZED MEDICATION

CROSS-REFERENCE TO RELATED APPLICATIONS

This application claims the benefit of U.S. Provisional Application No. 61/134,804, filed 13 Jul. 2008, and U.S. Provisional Application 61/201,362 filed 9 Dec. 2008, both of which are hereby incorporated by reference in their entirety.

FIELD OF THE INVENTION

The present invention relates to methods and apparatus for delivering a dose of aerosolized medication for inhalation by a patient into the lungs utilizing an inhaler which incorporates one or more vortex creating elements. These elements create a helical airflow pattern having a high tangential velocity within the central conduit of the inhaler, slowing and entraining the aerosol, increasing its residence time in the inhaler with the net result being an increase in the amount of drug delivered to the targeted biospace in conductive airways and lungs.

BACKGROUND OF THE INVENTION

Aerosols are increasingly being used for delivering medication for therapeutic treatment of the lungs. For example, in the treatment of asthma, inhalers are commonly used for delivering bronchodilators such as $\beta_2$ agonists and anti-inflammatory agents such as corticosteroids. Two types of inhalers are in common use, metered dose inhalers (MDIs) and dry powder inhalers (DPIs). Both types have as their object the delivery of medication, which is typically in the form of a solid particulate or powder, into the airways of the lungs at the location of the condition being treated.

In the MDI device, the medication is provided by the pharmaceutical manufacturer in a pressurized aerosol canister, with the medication being suspended or dissolved in a liquid propellant such as a hydrofluoroalkane (HFA) or chlorofluorocarbon (CFC). The canister includes a metering valve having a hollow discharge stem which can be depressed inward into the canister to discharge a metered volume of propellant-medication mixture in the form of an aerosol comprising fine droplets of propellant in which particles of the medication are suspended or dissolved. A typical MDI for use with such a canister includes a housing having an actuator and nozzle. The canister is inserted into the housing with the hollow discharge stem of the canister being received in a bore in the actuator. Depressing the closed end of the canister causes the stem to be pushed inward into the canister so that a metered volume of drug-containing propellant formulation is discharged through the nozzle resulting in an aerosol plume comprised of drug-containing propellant droplets or drug particles (the Aerosol Bolus). The housing further defines a flow path in fluid communication with the nozzle, the flow path having an outlet at a mouthpiece portion of the housing, such that the aerosolized medication may be inhaled after it exits the mouthpiece portion. The patient either inserts the mouthpiece into the mouth with the lips closed around the mouthpiece, or holds the mouthpiece at a slight distance away from an open mouth. The patient then depresses the canister to discharge the medication, and simultaneously inhales the Aerosol Bolus.

As used herein, the terms plume, medicament plume, discharge plume and similar terms are synonymous with Aerosol Bolus.

Several current versions of the pMDI include automatic actuators in which the breathing through the device causes the discharge of an Aerosol Bolus. These are termed Breath Actuated pMDIs or BApMDIs.

Most pMDIs have poor delivery efficiency—the ratio of drug delivered to the lungs divided by the nominal or metered dose. Typically pMDIs deliver less than 20 percent of the metered or nominal dose to the targeted biospace. Poor delivery efficiency is caused by a number of factors. One of these is incomplete evaporation of propellant in the Aerosol Bolus, resulting in a large portion of the metered dose being delivered in large droplets or particles which cannot be inhaled into the lungs. For effective delivery of the Aerosol Bolus to the conductive airways (bronchi, and subbronchioli) and the deep lungs (alveolar region), it is desirable that most of the drug-containing aerosol particles or droplets should have velocities matching that of the inspired breath at the mouth—preferably less than 300 centimeters per second to avoid impaction in oropharyngeal cavity, and less than 150 centimeters per second to avoid impaction in the trachea and bronchi. Additionally the aerosol droplets or particles which are inspired, should be less than about 10 microns ($10^{-5}$ meters) mass median aerodynamic diameter (MMAD) in size to avoid deposition in the oropharyngeal cavity, and preferably should be between about 1 micron and 5 microns MMAD to deposit in the lungs and conductive airways. Incomplete evaporation of propellant at the outlet of the mouthpiece results in a substantial fraction of the metered dose being delivered in the form of relatively large drug-containing propellant droplets or particles with the majority having MMADs greater than 10 microns.

Another factor contributing to poor delivery efficiency is high linear velocity and trajectory of the aerosol plume as it exits the mouthpiece. Ideally, the velocity of the aerosol should match the velocity of the patient's inspired breath so that the particles are entrained in the breath and carried into the lungs. But with most commercial pMDIs, the exit velocity of the aerosol substantially exceeds the velocity of the patient's breath. Most discharge the aerosol plume at high velocity, often exceeding 2000 centimeters/second, in a straight line trajectory, at a distance less than 10 centimeters from the back of the throat. Such droplets cannot be entrained in the patient's breath and efficiently inspired because their momentum—the product of their mass and velocity—is too high. A factor contributing to the poor delivery efficiency of most existing MDIs is excessive length of the plume or bolus of aerosol exiting the device. In most existing MDIs, this length typically exceeds 25 centimeters, and the aerosol plume is discharged typically less than 10 centimeters from the back of the throat which makes it difficult for the patient to inhale the entire bolus.

The large, high velocity aerosol droplets or particles generated by most pMDIs tend to impact the inside of the mouth and at the back of the patient's throat, with the result that much of the medication is swallowed and only a small fraction is delivered beyond the oropharyngeal cavity. The local concentration of medication in the mouth and throat can cause local side effects such as immunosuppression resulting in infections such as thrush development of fungal infections in the case of corticosteroids. Additionally, swallowing the drugs can lead to systemic absorption resulting in undesired systemic side effects. For example $\beta_2$ agonists, a common medicament delivered by MDI's, cause undesired heart rate increases, blood pressure elevation, muscle tremors, restlessness and insomnia when absorbed systemically via gastrointestinal absorption. Further, the wasted medication has been estimated to cost U.S. patients about $750 million per year.

In an effort to decrease plume velocity, some MDI designers have added tubular high volume spacers between the inhaler mouthpiece and the patient's mouth. Examples include spacers from Trudell, Astra and others. Although spacers improve delivery efficiency, most of the drug which is discharged from the inhaler impacts and sticks on inner surfaces of the spacer, and is therefore unavailable for inhalation by the user. Thus, MDIs with spacers still suffer from unacceptably low delivery efficiencies.

Accordingly, it has been an object of the present invention to provide a method and inhaler apparatus for delivering an aerosolized medication in which the respirable fraction of the metered dose i.e., the fraction in the form of particles or droplets (Aerosol Bolus) that are respirable, having at a minimum, an MMAD of less than 10 microns, an preferably an MMAD between about 1 and about 5 microns, at the exit of the inhaler apparatus.

It has been a further object of the present invention to provide a method and apparatus for delivering an aerosolized medication in which the linear velocity of the Aerosol Bolus at the exit of the apparatus approximately matches the velocity of the patient's inspired breath.

It has been another object of the invention to maximize dispersion and mixing of the drug-containing aerosol particles or droplets (Aerosol Bolus) in the inspiratory breath within an inhaler apparatus.

It has been a still further object of the present invention to provide a method and apparatus for delivering an aerosolized medication in which the length of the bolus of aerosolized medication which exits the apparatus is as short as possible and in which the Aerosol Bolus has a nonlinear trajectory A further object of the invention has been to provide a method and apparatus for maximizing the evaporation of liquid propellant in an inhaler.

Still another object of the invention has been to provide a method and apparatus for delivering an aerosolized medication in which impaction and sticking of medication on the inner walls of the apparatus is minimized by providing multiple vortex elements along the entire path of the plume from where is exits the discharge stem of the metering valve to where it exits the mouthpiece.

SUMMARY OF THE INVENTION

The above and other objects of the invention are achieved by the methods and apparatus of the invention in which flow control techniques and devices are used to promote mixing of the drug containing aerosol droplets or particles (the Aerosol Bolus) with the inspiratory air, to impart a swirling motion to the Aerosol Bolus by have one or more of three separate vortex generating elements disposed along the entire path taken by plume. The vortex motion imparted to the plume increases evaporation of propellant, slows down the Aerosol Bolus before it reaches the exit of the apparatus, reduces the impaction of aerosol on the inner walls of the apparatus, and aids in synchronizing the flow rate of the plume to match that of the inspiratory breath.

A general discussion of the metered dose inhalers having the same general design as discussed herein, is provided in U.S. Pat. No. 5,954,047—Methods and Apparatus for Delivering Aerosolized Medication; U.S. Pat. No. 6,026,808—Methods and Apparatus for Delivering Aerosolized Medication; and U.S. Pat. No. 6,095,141—Methods and Apparatus for Delivering Aerosolized Medication.

More specifically, the invention provides a metered dose inhaler apparatus including a housing adapted to support a pressurized canister, the housing having an actuator and nozzle assembly with a bore adapted to receive the hollow outlet stem of the canister, the housing further including a generally tubular conduit having an open end forming a mouthpiece adapted to be inserted into the mouth of a user, a nozzle discharge orifice of the actuator and nozzle assembly being positioned to direct an Aerosol Bolus into the conduit.

Optionally, the inhaler may include an air tube supported within the conduit and having an air tube outlet arranged opposite the nozzle discharge orifice and the air tube inlet in fluid communication with ambient air outside the conduit, the air tube being oriented so that air flowing out of the air tube outlet is directed so as to impinge on a plume of aerosolized medication discharged from the canister through the nozzle discharge orifice. Thus, an inspiratory effort exerted on the mouthpiece causes air to flow into the air tube inlet and out the air tube outlet to impinge on the plume and thereby enhance dispersion and mixing of the medication within the conduit. The air jet from the air tube also causes the plume to slow down so that the velocity of the aerosol exiting the device approximately matches the velocity of a patient's inspired breath.

The inspiratory breath of the patient, in addition to causing air flow through the impinging jet, also causes air to flow through one or more of: a back plate, a back wall and spacer tube. Though the air flow described herein is derived from the inspiratory breath of a patient, any means of providing a pharmacologically-safe flow of gas can used to impart a vortexing motion to the plume.

These three elements are disposed within the conduit to provide vortexing motion to the medicament plume as it travels from the discharge nozzle to the mouthpiece.

The vortexing back plate is formed behind the discharge stem of the metering valve and assists in preventing the Aerosol Bolus from getting trapped in the closed end of the conduit. The second element, the vortexing backwall, is positioned near the discharge nozzle. The third element, a non-porous tangential flow spacer, is positioned just inside the inner walls of the conduit. In one embodiment, the tangential flow spacer has a general hollow cylindrical shape that has tangential slits of varying shape and configuration disposed along most of the length of the tangential spacer. The combination of vortex creating elements along most of the length of the conduit increases the flow path of the plume and greatly slows it down. Slowing down the plume also increases the residence time of the aerosol within the apparatus and leads to a shorter bolus to be inhaled. The increased mixing and residence time promote more complete evaporation of propellant at the exit of the mouthpiece which results in particles of more efficacious size.

In one embodiment of the invention, an optional air tube is arranged to direct an air jet away from the open end of the mouthpiece so as to impinge on the plume. The air tube is supported within the conduit by one or more hollow spokes connected to the wall of the conduit, with the hollow passage of each spoke being connected at one end to a corresponding passage through the conduit wall to ambient air outside the conduit and at the other end to the inlet of the air tube. When the patient inhales on the open end of the mouthpiece, air is drawn into the air tube to cause an air jet to exit the air tube. Once this air jet has been established, the canister is actuated to discharge an Aerosol Bolus toward the air jet. The Aerosol Bolus and air jet meet, causing mixing and deceleration of the Aerosol Bolus.

To reduce impaction and sticking of medication on the inner walls of the apparatus, the invention provides an aerosol flow control apparatus, useful for either MDI or DPI devices, including a housing defining a conduit, the conduit having an open end defining a mouthpiece and a substantially closed end defined by a vortexing back plate remote from the mouthpiece, with a medication dispenser assembly being arranged within the housing to direct medication into the conduit. The medication dispenser may be a pressurized canister with actuator and nozzle, or alternatively may be a dispenser for medication in dry powder form. The vortexing back plate, which includes a first set of vortexing air inlets in fluid communication with ambient air outside the conduit, is disposed such that the first set of vortexing air inlets opens into the conduit adjacent the inner wall of the conduit, in a direction generally toward the open end of the mouthpiece. The first set of vortexing air inlets is located directly behind the discharge stem of the metering valve and the inlets angled so as to impart a vortexing motion to the ambient air which is drawn in through the first set of vorteing air inlets. This vortexing motion helps to reduce any possible dead space behind the discharge stem and will start to impart a vortexing motion to the plume as it travels down the conduit toward the mouthpiece. The vortexing back plate fixedly attaches to the vortexing backwall. The vortexing backwall has one end which attaches to the open end of the conduit and then narrows down to a smaller size opening adapted to receive the vortexing back plate. Disposed about the periphery of the vortex ing backwall is the second set of vortexing inlets. The auxiliary air flow acts as a buffer or boundary layer flow along the inner walls of the conduit, reducing the likelihood of the Aerosol Bolus impacting and permanently sticking to the inner walls. The vortex generators preferably comprise inwardly directed vanes which are oriented at an angle to the axial direction so as to impart swirl and vorticity to the air flowing over them.

BRIEF DESCRIPTION OF THE DRAWINGS

The accompanying drawings, which are incorporated in and constitute a part of this specification, illustrate various embodiments of the invention and, together with the general description of the invention given above and the detailed description given below, serve to explain the principles of the invention.

FIGS. 9A, 9B and 9C are the X-cut, Y-cut, and Z-cut respectively for a tangential spacer having slits along 75% of the length. FIGS. 9D, 9E and 9F are the X-cut, Y-cut and Z-cut respectively for a tangential spacer having elongated slits.

DETAILED DESCRIPTION OF THE DRAWINGS

Figure 1:
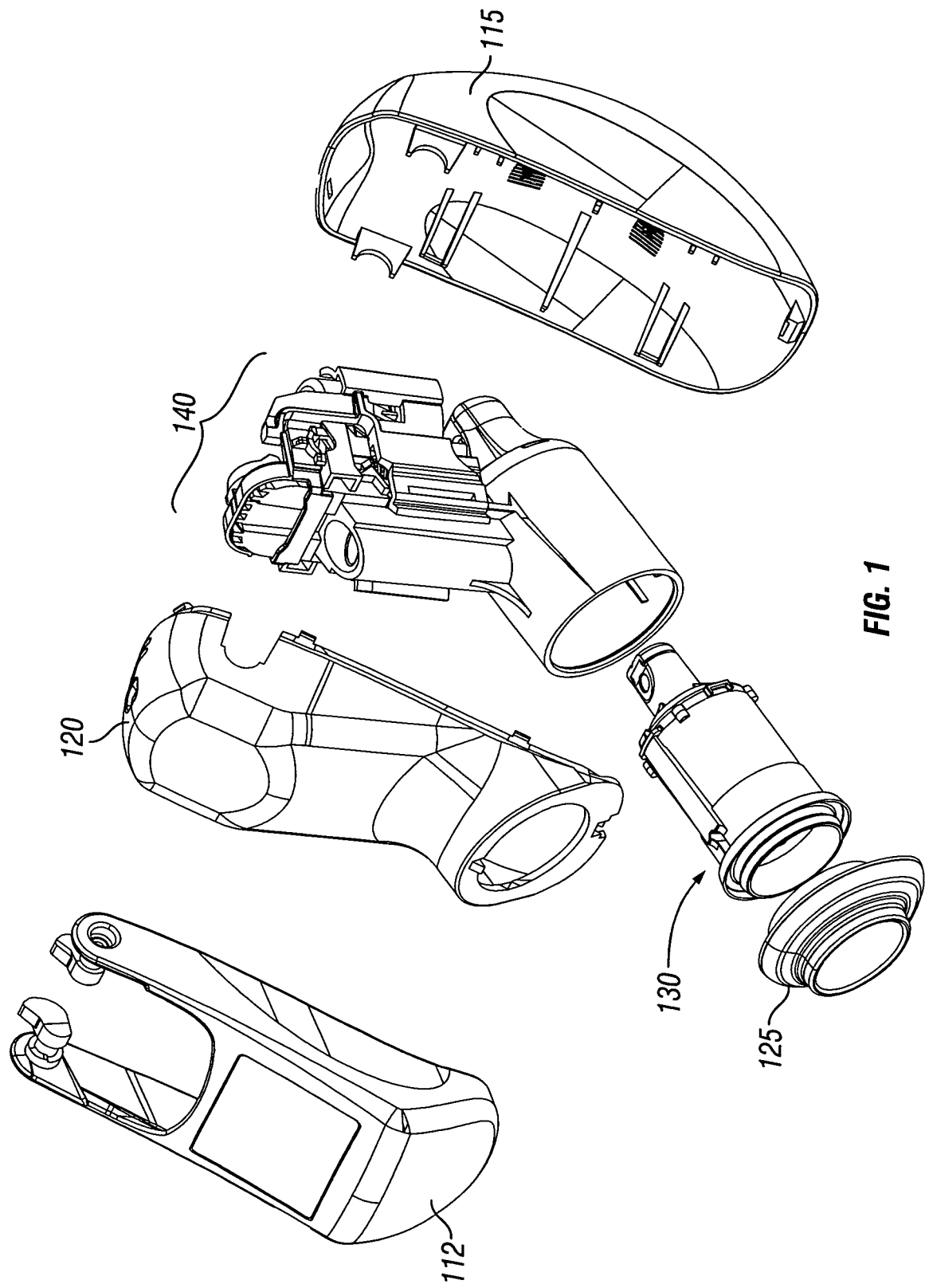
FIG. 1 is an exploded perspective view of an inhaler which can incorporate elements of the present invention

FIG. 1 depicts a general embodiment of an Inhaler 100 in accordance with the principles of the invention. The inhaler 100 includes a Cover 112, Front Housing 120, Back Housing 115, Dispensing Assembly 140, Flow Control Chamber 130 and Mouthpiece 125. The inhaler apparatus of the present invention is usable with any standard pressurized canister having an internal metering valve with a hollow discharge stem which may be depressed inwardly with respect to the canister body from an inoperative position in which discharge of medication is prevented, to an operative position in which a metered volume of the canister contents is discharged through the hollow discharge stem.

Figure 2:
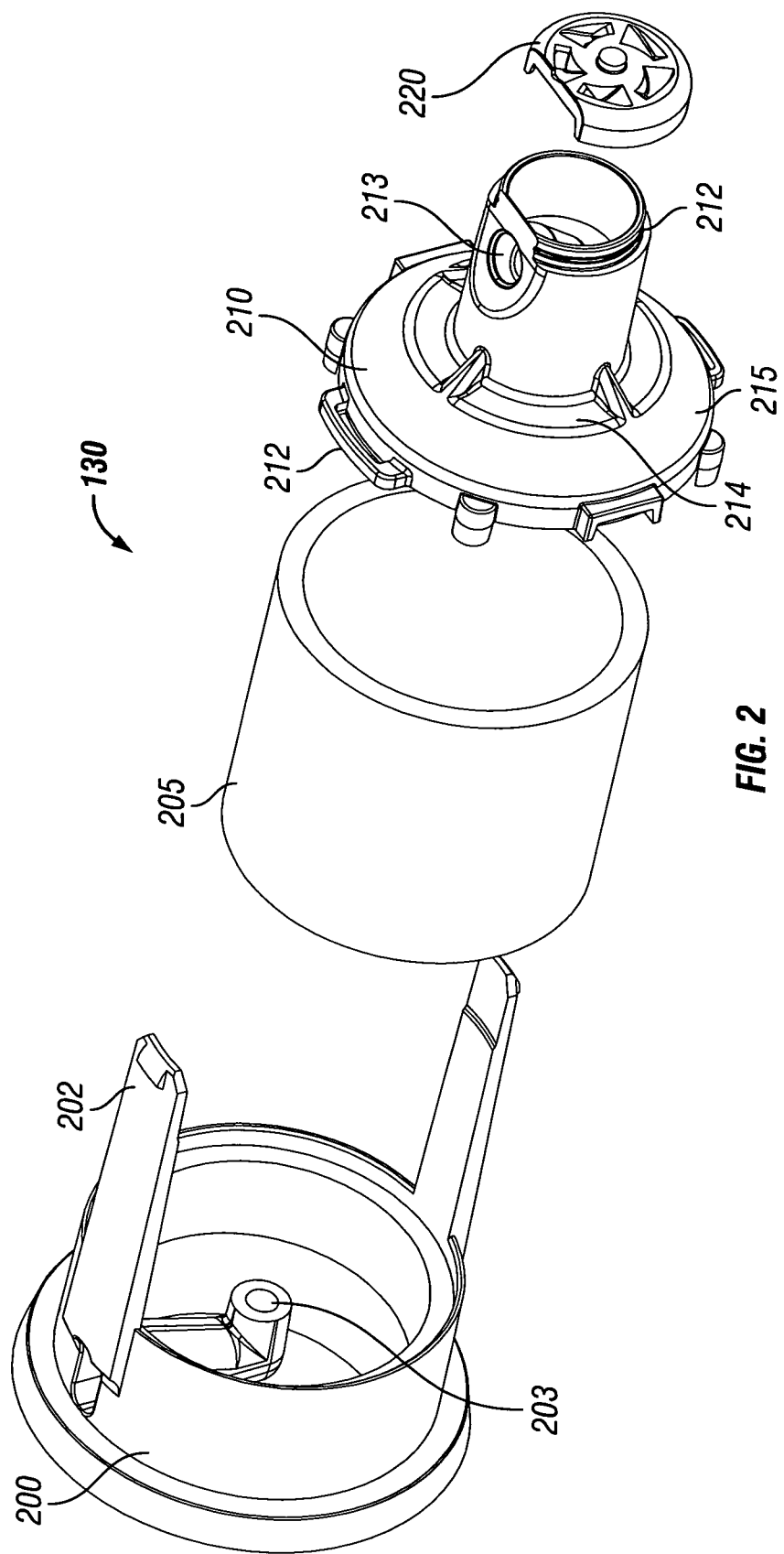
FIG. 2 is an exploded perspective view of the flow control chamber showing the internal components.

FIG. 2 shows an exploded view of the Flow Control Chamber 130 which consists of the Impinging Jet Housing 200, Porous Spacer 205, Backwall 210 and Vortexing Back Plate 220.

Impinging Jet Housing 200 has two Attachment Arms 202 which lock into Tabs 212 on Backwall 210. Impinging Jet 203 is mounted in the middle of the Impinging Jet Housing 200 and directed towards and opposite to the direction of the medicament plume discharged from the canister. The valve stem of the medicament canister valve is disposed within Valve Stem Opening 213. Incoming air is directed to the Impinging Jet 203 by entering through Air Inlet 204 which directs the air to and out of the Impinging Jet 203.

Porous Spacer 205 is held rigidly in place by being captured between Impinging Jet Housing 200 and Backwall 210. Vortexing Back Plate 220 fixedly attaches to the Narrow End 212 of Backwall 210. Backwall 210 has Openings 214 disposed about its periphery in Transition Surface 215, which transitions from the wide end to the narrow end of Backwall 210. Openings 214 are merely straight openings and do not impart any vortexing motion to the incoming air stream or to the Aerosol Bolus.

FIG. 2 shows one embodiment of the present invention in which there is one vortexing element shown. Spacer 205 and Backwall 210 can be substituted with a vortexing element. Details of those vortexing elements are described below.

Figure 3:
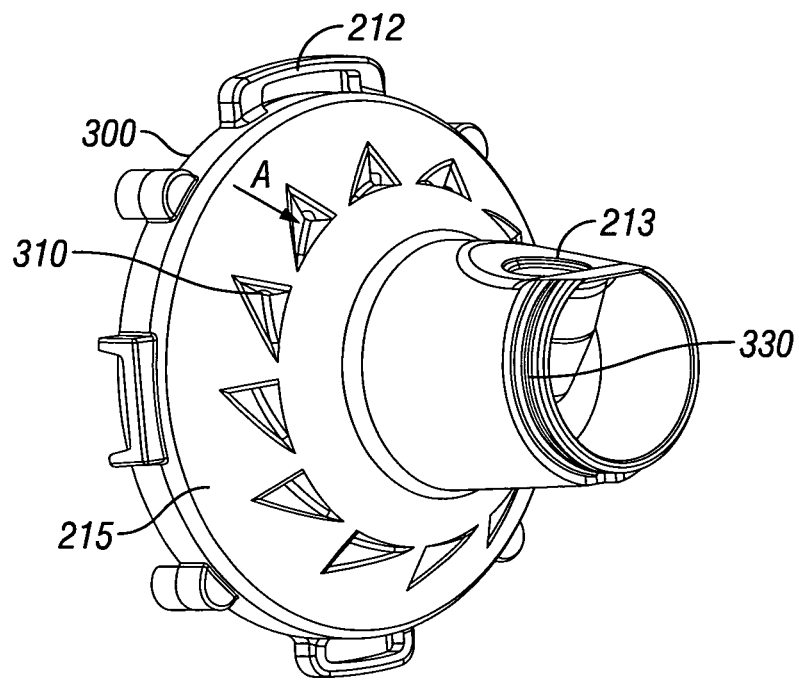
FIG. 3 is a perspective view of one embodiment of a vortexing backwall of the present invention.

FIG. 3 shows one embodiment of the Vortexing Backwall 300 of the present invention. The Second Set of Vortexing Air Inlets 310 is disposed peripherally around the Transition Surface 215. The Second Set of Vortexing Air Inlets 310 is comprised of a plurality of vortexing openings. As shown in this embodiment, the Second Set of Vortexing Air Inlets 310 are openings that are triangular in shape such that the air flow is in the direction of Arrow A, and which imparts a vortexing motion to the incoming air which further imparts a vortexing motion to the medicament plume discharged from the valve stem. The exact shape, configuration, number and position of the air inlets of the Second Set of Vortexing Air Inlets 310 may be varied, and such variations are within the scope of the invention.

Figure 4:
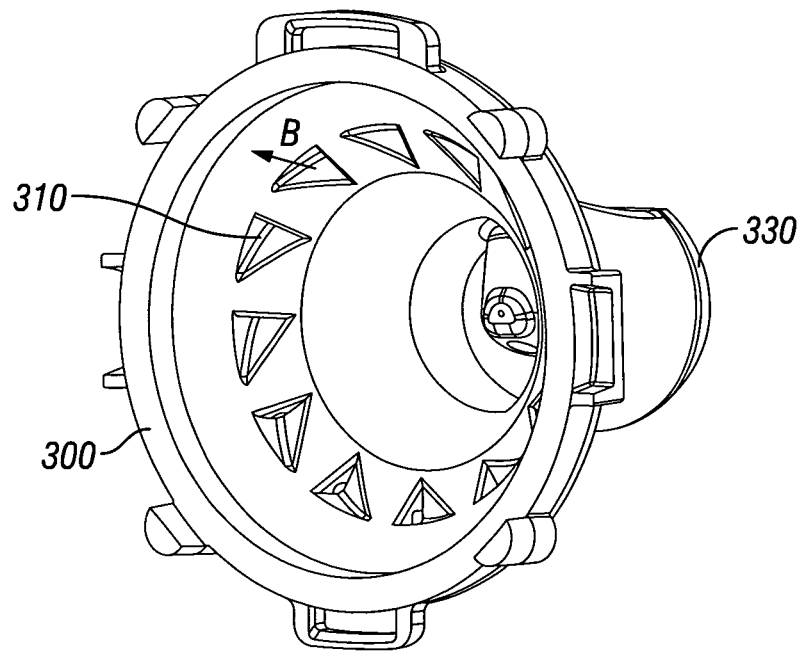
FIG. 4 is a perspective view of one embodiment of a vortexing backwall as shown in FIG. 3, but rotated about 180 degrees around the vertical axis.

FIG. 4 shows the same embodiment of the Vortexing Backwall 300 as shown in FIG. 3, but rotated about 180 degrees about the vertical axis in order to view the other side. Air enters into the inside of the Vortexing Backwall 300, through the vortex openings in the direction shown by Arrow B.

Figure 5:
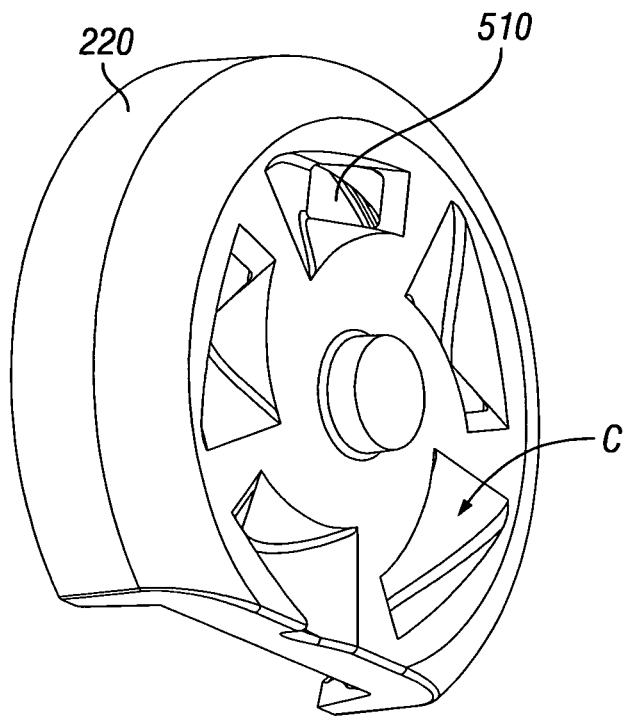
FIG. 5 is perspective view of one embodiment of the vortexing end plate of the present invention.

FIG. 5 shows Vortexing Back Plate 220 with the First Set of Vortexing Air Inlets 510 disposed about the periphery of Vortexing Back Plate 220. The First Set of Vortexing Air Inlets 510 is comprised of a plurality of vortexing openings.

Ambient air is drawn through Vortexing Back Plate 220 in the direction shown by Arrow D. The exact shape, configuration, number and position of the air inlets of the First Set of Vortexing Air Inlets 510 may be varied, and such variations are within the scope of the invention.

Figure 6:
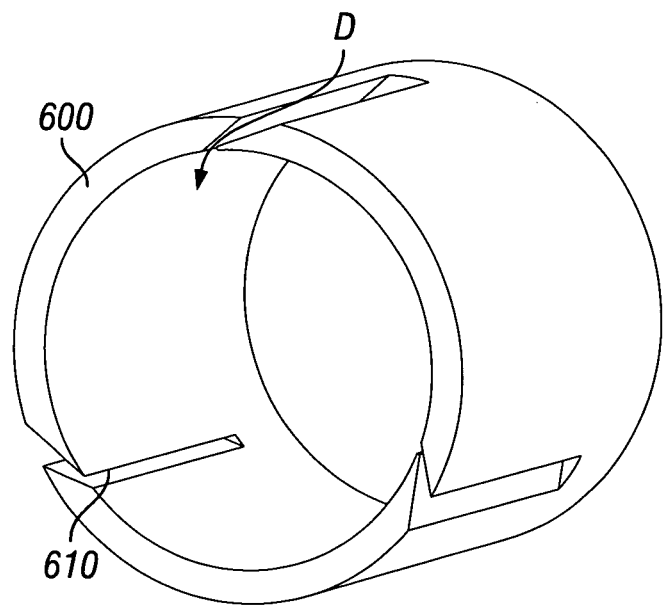
FIG. 6 is a perspective view of one embodiment of a tangential flow spacer of the present invention.

FIG. 6 shows one embodiment of the Tangential Flow Spacer 600 which replaces Porous Spacer 205 in an embodiment of Flow Control Chamber 130 of the present invention. Unlike Porous Spacer 205, Tangential Flow Spacer 600 is made of any non-porous material, including but not limited to plastics such as polyethylene, polypropylene, and delrin.

A plurality of Tangential Slits 610 is disposed about the periphery of the Tangential Flow Spacer 600. Air is drawn into the interior of the Tangential Flow Spacer 600 along the path shown by Arrow D. The Tangential Slits 610 impart a vortexing motion to the incoming air which further imparts a vortexing motion to the medicament plume discharged from the valve stem.

Figure 7:
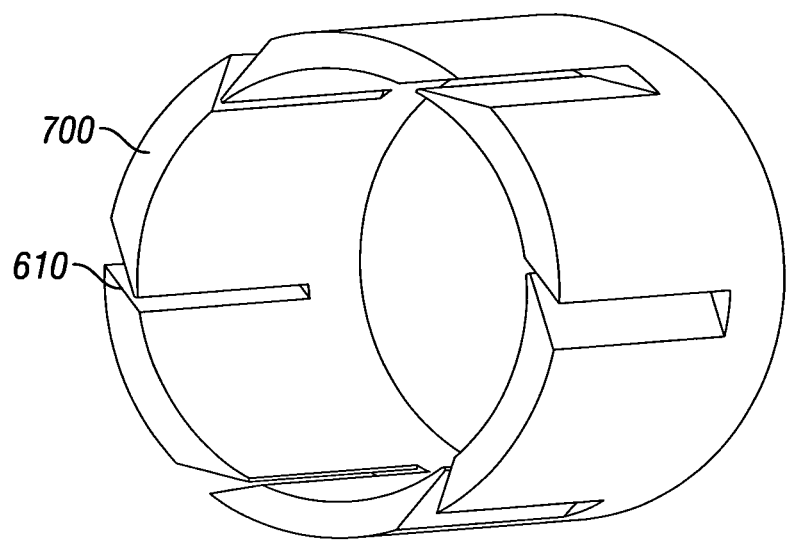
FIG. 7 is a perspective view of a second embodiment of the tangential flow spacer of the present invention.

FIG. 7 shows Tangential Flow Spacer 700, another embodiment of this element of the present invention. In this case, there are 6 Tangential Slits 610 located along the periphery of Tangential Flow Spacer 700.

In order to maintain physical rigidity, the Tangential Slits 610 cannot extend completely along the full length of the Tangential Flow Spacer 600 or 700. In the two embodiments shown in FIGS. 6 and 7, the slits extend for about 75% of the length of the Tangential Flow Spacers 600 and 700.

However, variations of this design are within the scope of the invention which includes such variations as having alternating lengths of the Tangential Slit 610, with a first slit being relatively long, for example 80% of the length of the Tangential Flow Spacer 600 or 700 and the next slit being shorter, for example 50% and then alternating back and forth between the longer length and the shorter length. Other variations would include alternating between three lengths or slowly increasing lengths or even between random lengths.

Other variations of the vortexing inlets could include the triangular shaped opening as previously described for the Vortexing Backwall, slanted circular openings, slanted ellipsoid openings, or any other configuration which imparts a tangential, vortexing motion to the incoming air.

Figure 8:
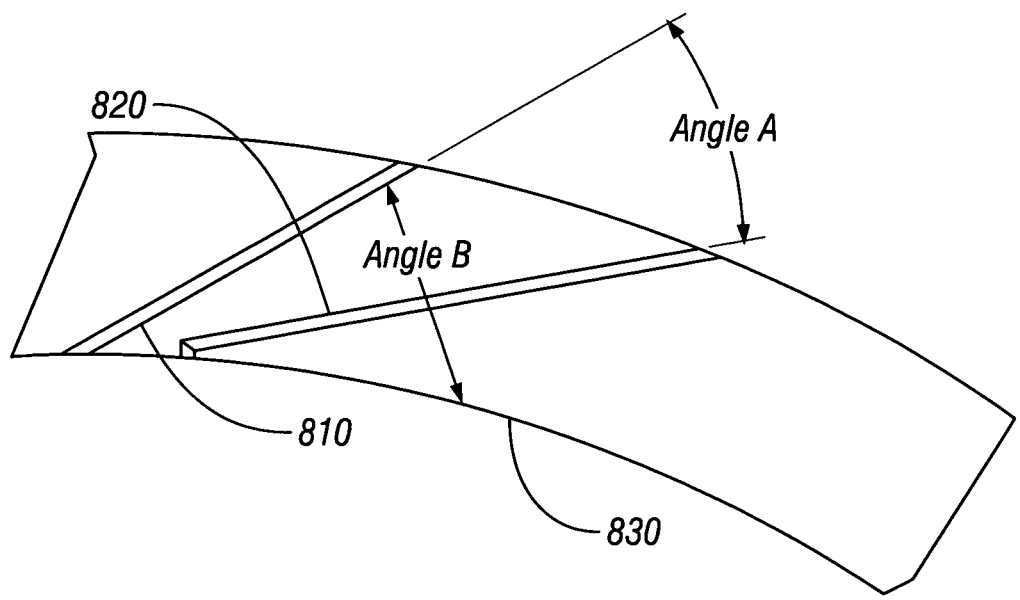
FIG. 8 is perspective close-up view of one embodiment of a tangential slit in the tangential flow spacer of the present invention.

FIG. 8 shows a cutaway view through one of the Tangential Slits 610 as shown in FIGS. 6 and 7. Angle A is the angle between First Wall 810 and Second Wall 820. Angle B is the angle between First Wall 810 and Inner Wall 830 of a Tangential Flow Spacer such as 600, 700 or other embodiments of this element of the invention.

Angle A is primarily dictated by manufacturing concerns, in particular removal from an injection mould. However, within the range that Angle A can take on for manufacturing concerns, specific values may be selected to achieve the level of vortexing motion desired.

The value of Angle B strongly influences the vortex creating capabilities of the various openings that can be incorporated in the Tangential Flow Spacer. Angle B can be in the range of about 85 to about 5 degrees.

Though discussed here in relation to the Angle B of the Tangential Flow Spacer, The First Set and Second Set of Vortexing Inlets also make an Angle B with respect to the respective inner surfaces of the Vortexing End Plate and the Vortexing Back Wall respectively. Both of those Angle B's are also in the range of about 85 to about 5 degrees.

Figure 9B:
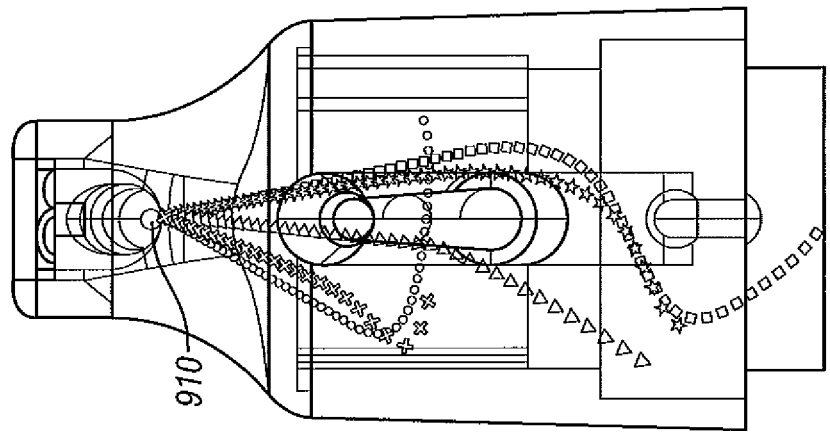
FIGS. 9A-9F depict a computational fluid dynamic simulation that shows the entrainment, vortexing and tangential flow imparted by the embodiments of the instant invention on an ethanol/propellant blend Aerosol Bolus.
Figure 9A:
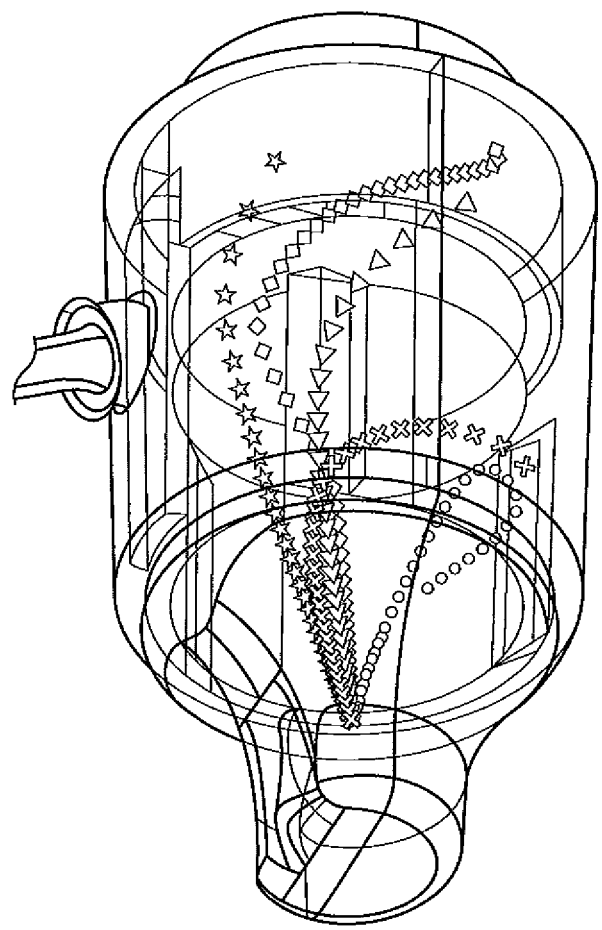
Figure 9C:
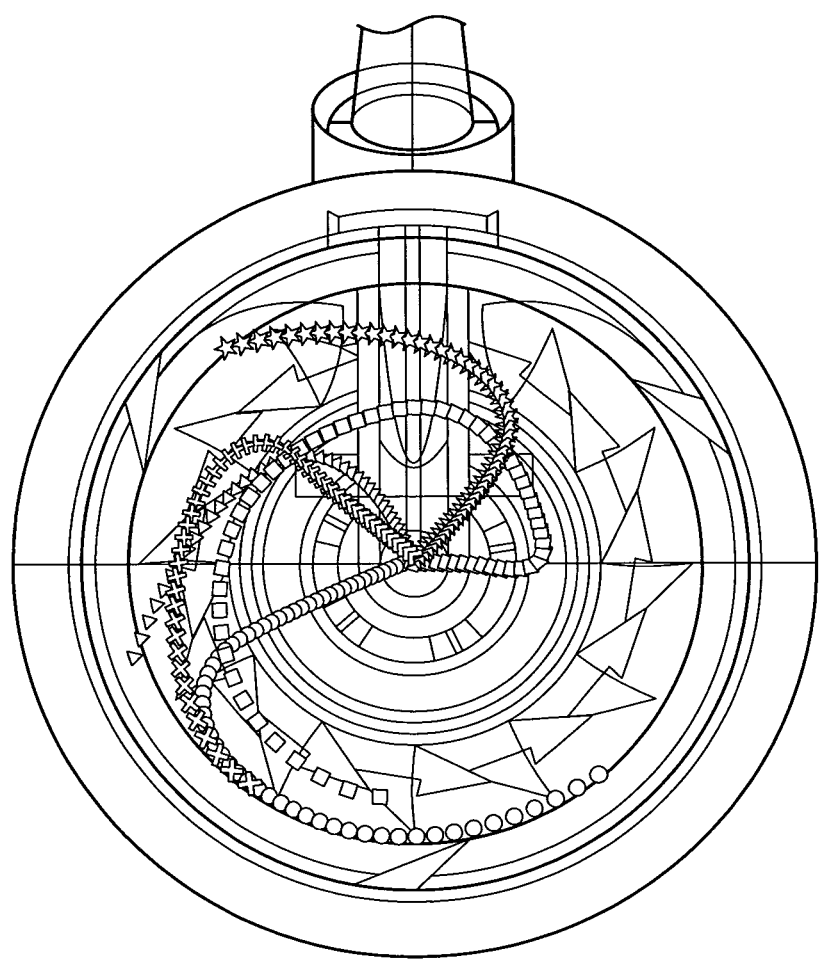
Figure 9E:
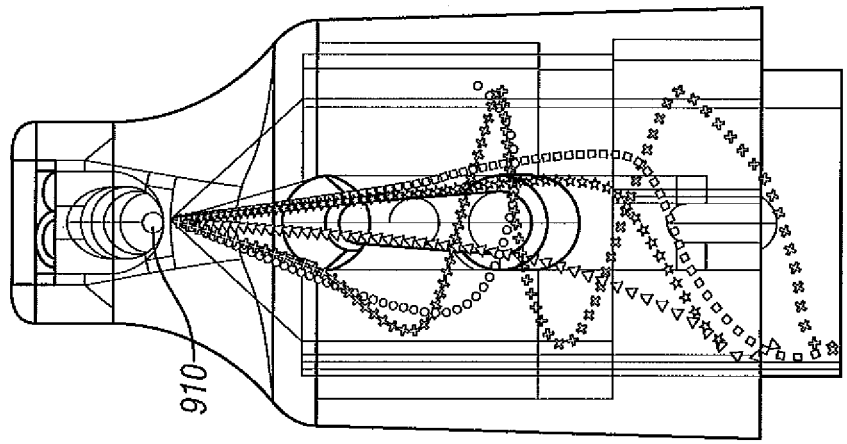
Figure 9D:
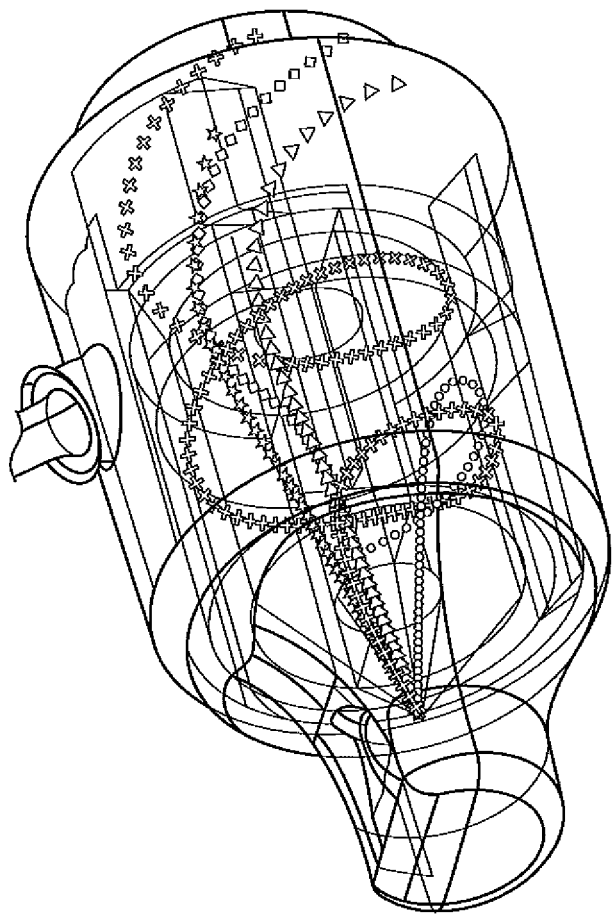
Figure 9F:
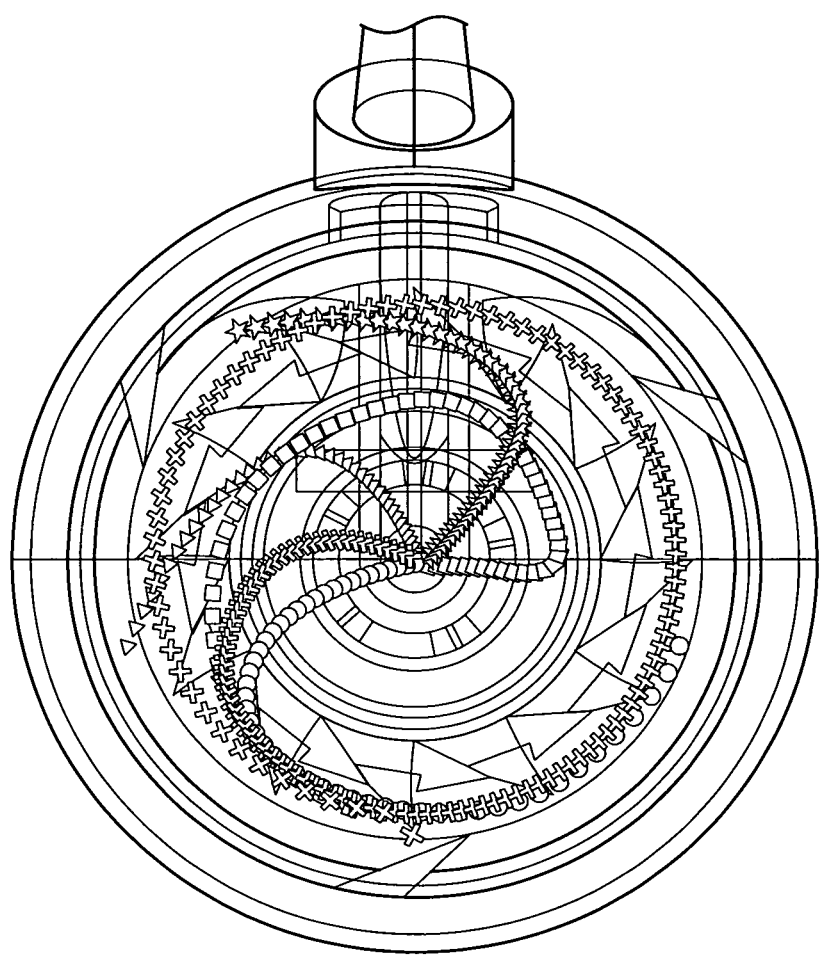

FIGS. 9A-9F depict a computational fluid dynamics simulation of the effects of one embodiment of the Tangential Flow Spacer on an ethanol/HFA propellant Aerosol Bolus. FIGS. 9A-9C are based on the Tangential Flow Spacer having slits that are 75% of the length of the Tangential Flow Spacer. FIGS. 9D-9F are based upon slits which are almost the entire length of the Tangential Flow Spacer. It should be noted that such a spacer would be difficult if not impossible to actually fabricate, but can be the subject of the computer modeling. FIGS. 9A and 9D are X cut. FIGS. 9B and 9E are Y cut and show the medicament discharge element 910.

The Aerosol Bolus discharges from the nozzle (FIGS. 9B and 9E, 910) on the left hand side of the X-cut, the top of the Y-cut and in the center of the Z-cut sections as depicted by the four dotted line vectors. Note the initial straight line trajectory of the Aerosol bolus vectors as they leave the discharge nozzle with an angle of approximately 20 degrees off the centerline of the central conduit. As the vectors move down the conduit towards the mouthpiece, the Tangential Flow Spacer imparts a vortexing pattern on the vectors causing them to develop a tangential velocity as shown by the helical swirl pattern. By the time they reach the mouthpiece exit their trajectory has changed from one that was initially coplanar with the conduit axis to one that is curling around the conduit axis. As can be observed by tracing the trajectories, the vectors have curled between ½ to 2 full turns around the axis. This effective increases their path length out of the device by between about 70% and about 300% with a proportional increase in residence time. The increased path length slows the Aerosol Bolus and provides more time for the propellant to evaporate. Both effects decrease the momentum of the Aerosol Bolus and increase the probability of entrainment in the inspiratory breath. The decrease in momentum also renders the Aerosol Bolus more respirable.

In summary, the present invention comprises an inhaler which can deliver a metered dose from a pressurized medicament canister or a dry powder generator and delivery it along a conduit to a mouthpiece. The conduit comprises one or more vortexing elements disposed along the length of the conduit. Preferably vortexing elements are disposed along a significant portion of the conduit and most preferably along essentially all of the length of the conduit. The vortexing elements can be one of several configurations. However, all of the vortexing elements have disposed within, one or more vortex openings which may be of various configurations all of which impart a vortexing motion to air flowing through the openings and which impart a vortexing motion to the medicament plume. The vortexing opening configurations include, but are not limited to: slits, slots, openings of any shape and with openings penetrating the vortexing elements at various angles. The vortexing openings can also be vanes which may protrude inwardly or outwardly.

The vortexing elements may include, but are not limited to a hollow cylindrical tangential flow spacer, a vortexing backwall which provides a connection between the pressurized canister and the flow spacer and a vortexing back plate which is attached to a second end of the vortexing backwall.

Though shown herein, as three mechanically separate components, one of more of the vortexing elements may be combined as a single integral component.

Further, additional components maybe utilized. For example, the tangential flow spacer could be made up of two flow spacers, each potentially having a different design of vortexing openings in order to enhance the vortexing action.

Although the inventive elements have been discussed primarily in relation to imparting vortexing motion to the discharge plume from a MDI, the same inventive concepts and embodiments can be utilized with dry powder inhalers.

While the present invention has been illustrated by a description of various embodiments and while these embodiments have been described in considerable detail, it is not the intention of the applicants to restrict or in any way limit the scope of the invention to these embodiments. Though shown and discussed as three separate elements, any arrangement or number of vortexing elements which provides a vortexing action to the medicament plume during the entire time the plume travels, from valve stem discharge to mouthpiece, is within the scope of the invention.

I claim:

1. A pressurized metered dose inhaler which delivers a bolus of medicament into an air flow caused by the inspiratory breath of a patient comprising:

a flow control chamber having a primarily open end and a primarily closed end, wherein the patient causes an inspiratory air flow by breathing through said primarily open end of said flow control chamber;

a medicament discharge element adapted to deliver a bolus of said medicament into said flow control chamber immediately before or during patient's inspiratory breath; and one or more vortexing elements disposed within or comprising part of said flow control chamber and adapted to have some portion of said inspiratory air flow through openings in said vortexing elements wherein said openings impart a tangential velocity to said inspiratory air flow and create a helical swirl pattern to said inspiratory air flow and to said medicament bolus, wherein said one or more vortexing elements comprises a vortexing back plate disposed at the primarily closed end and wherein said medicament bolus is introduced into the inspiratory air flow between said vortexing back plate and said primarily open end of said flow control chamber;

and wherein the flow rate of said medicament bolus when it reaches the primarily open end of said flow control chamber has been slowed and approximately matches the air flow of said inspiratory air flow.

2. The pressurized metered dose inhaler as described in claim 1 wherein one of said one or more vortexing elements is disposed immediately downstream from the location where said medicament bolus is introduced into the inspiratory air flow.

3. The pressurized metered dose inhaler as described in claim 1 wherein one of said one or more vortexing elements is disposed at the primarily open end of said flow control chamber.

4. The pressurized metered dose inhaler as described in claim 3 wherein said vortexing element is tubular in shape and comprises one or more slits in the wall of side vortexing element.

5. The pressurized metered dose inhaler as described in claim 4 wherein said tubular vortexing element is non-porous.

6. The pressurized metered dose inhaler as described in claim 4 wherein said one or more slits form an angle B with respect to the side wall of said tubular vortexing element, wherein angle B is in the range of about 5 degrees to about 85 degrees.

7. The pressurized metered dose inhaler as described in claim 6 wherein said slit is oriented essentially along the longitudinal axis of the tubular vortexing element.

8. The pressurized metered dose inhaler as described in claim 1 is comprised of three vortexing elements.

9. The pressurized metered dose inhaler as described in claim 8 wherein said three vortexing elements are a single integral component.

10. The pressurized metered dose inhaler as described in claim 1 wherein the mass median aerodynamic diameter (MMAD) of the medicament bolus as it exits the primarily open end of the flow control chamber is less than about 10 microns.

11. The pressurized metered dose inhaler as described in claim 10 where the MMAD of the medicament bolus as it exits the primarily open end of the flow control chamber is in the range of about 1 micron to about 5 microns.

12. The pressurized metered dose inhaler as described in claim 1 wherein the flow rate of the medicament bolus as it exits the primarily open end of the flow control chamber is less than about 300 centimeters per second.

13. The pressurized metered dose inhaler as described in claim 1 wherein the flow rate of the medicament bolus as it exits the primarily open end of the flow control chamber is less than about 150 centimeters per second.

14. The pressurized metered dose inhaler as described in claim 1, wherein the pressurized metered dose inhaler is breath actuated.

15. A pressurized metered dose inhaler which delivers a bolus of medicament into an air flow cause by the inspiratory breath of a patient comprising:

a flow control chamber having a primarily open end and a primarily closed end, wherein the patient causes an inspiratory air flow by breathing through said primarily open end of said flow control chamber;

a medicament discharge element adapted to deliver a bolus of said medicament into said flow control chamber immediately before or during patient's inspiratory breath;

a first, a second and a third vortexing elements disposed within or comprising part of said flow control chamber and adapted to have some portion of said inspiratory air flow through openings in said vortexing elements wherein said vortex element impart a tangential velocity to said inspiratory air flow and create a helical swirl pattern to said inspiratory air flow and to said medicament bolus;

said first vortexing element is a vortexing back plate disposed at the primarily closed end of said flow control chamber wherein said medicament bolus is introduced into the inspiratory air flow between said vortexing back plate and said primarily open end of said flow control chamber;

said second vortexing element is disposed immediately downstream from the location where said medicament bolus is introduced into the inspiratory air flow;

said third vortexing element is tubular in shape and comprises one or more slits in the wall of said vortexing element and wherein said third vortexing element is disposed between said second vortexing element and said primarily open end of said flow control chamber;

wherein the flow rate of said medicament bolus when it reaches the primarily open end of said flow control chamber has been slowed and approximately matches the air flow of said inspiratory air flow.

16. The pressurized metered dose inhaler as described in claim 15, wherein the pressurized metered dose inhaler is breath actuated.

* * * * *